United States Patent [19]

Gratton et al.

[11] Patent Number: 5,323,010
[45] Date of Patent: Jun. 21, 1994

[54] TIME RESOLVED OPTICAL ARRAY DETECTORS AND CCD CAMERAS FOR FREQUENCY DOMAIN FLUOROMETRY AND/OR PHOSPHORIMETRY

[75] Inventors: Enrico Gratton, Urbana; Martin VandeVen; Beniamino Barbieri, both of Champaign, all of Ill.

[73] Assignee: I.S.S. (USA) Inc., Champaign, Ill.

[21] Appl. No.: 983,829

[22] Filed: Dec. 1, 1992

[51] Int. Cl.$^5$ ............................................. G01N 21/64
[52] U.S. Cl. .................................................. 250/458.1
[58] Field of Search ................. 250/461.1, 459.1, 458.1

[56] References Cited

U.S. PATENT DOCUMENTS

| 4,840,485 | 6/1989 | Gratton | 356/317 |
| 4,937,457 | 6/1990 | Mitchell | 250/458.1 |
| 5,212,386 | 5/1993 | Gratton et al. | 250/458.1 |

FOREIGN PATENT DOCUMENTS

| 242485 | 1/1987 | German Democratic Rep. | 250/458.1 |
| 245491 | 5/1987 | German Democratic Rep. | 250/458.1 |

OTHER PUBLICATIONS

Lakowicz et al., "Gigahertz Frequency-Domain Fluorometry: Applications to Picosecond Processess and Future Developments." *SPIE* vol. 909 Time-Resolved Laser Spectroscopy in Biochemistry (1988) pp. 15–22.

Laczko et al., "10-GHz frequency-domain fluorometer." *Rev. Sci. Instrum.* 61(9) (Sep. 1990). pp. 2331–2337.

Berndt et al., "4 GHz internal MCP-photomultiplier cross correlation." *Rev. Sci. Instrum.* 61(10) (Oct. 1990) pp. 2557–2565.

Gratton et al., "Parallel acquisition of fluorescence decay using array detectors." *SPIE* vol. 1204 Time-Resolved Laser Spectroscopy in Biochemistry II (1990) pp. 21–25.

Gratton et al., "A Continuously Variable Frequency Cross-Correlation Phase Fluorometer With Picosecond Resolution." *Biophysical Journal* vol. 44 (1983) pp. 315–324.

*Primary Examiner*—Constantine Hannaher
*Attorney, Agent, or Firm*—Gerstman, Ellis & McMillin, Ltd.

[57] ABSTRACT

An apparatus for cross-correlation frequency domain fluorometry-phosphorimetry comprises a source of electromatic radiation and means for amplitude modulating the radiation at the first frequency. The amplitude modulated radiation is directed at a sample, while an optical array detector measures the resulting luminescence of the sample. A signal is provided coherent with the amplitude modulated electromagnetic radiation signals, at a second frequency which is different from the first frequency. The apparatus has the capability for shutting off and turning on the coherent signal at the second frequency in a cycle which is at a third frequency that is different from the difference between the first and second frequencies. This produces a resultant signal at a frequency derived from the difference and the third frequency. The resultant signal, when turned on, modulates the gain of the detecting means or multiplies its output, depending upon the nature of the detecting means. The amount of luminescence measured by the optical array detector is read when the coherent signal is off in its cycle of the third frequency. A signal from the reader described above is then detected at a frequency of the resultant signal to determine phase shift and modulation changes of the luminescence.

20 Claims, 6 Drawing Sheets

TIME RESOLVED OPTICAL ARRAY DETECTORS AND CCD CAMERAS FOR FREQUENCY DOMAIN FLUOROMETRY AND/OR PHOSPHORIMETRY

BACKGROUND OF THE INVENTION

In Gratton U.S. Pat. No. 4,840,485, and numerous other references, a method is disclosed of performing cross-correlation frequency domain fluorometry and/or phosphorimetry. This technique is capable of obtaining sophisticated data about phase shifts and modulation changes of luminescence (including phosphorescence) by the use of an amplitude modulated excitation light at a first frequency for the material being tested, coupled with a detector where the gain is modulated at a different frequency. Data is recovered at the cross-correlation frequency, which is the difference between the above two frequencies.

In accordance with this invention, improvements are provided in the simultaneous measurement of the spectral intensity of the luminescence (phosphorescence) of a target material at a number of wavelengths, making use of optical array detector means for example. As is known to the art, an optical array detector can be made using a linear array of detectors or matrix of detectors such as a charge coupled device (CCD) or charge insulator device (CID) chip. For example, to obtain spectral information from the luminescence of a target material excited by a modulated beam of electromagnetic energy, these devices are placed at a focus of an aberration-corrected, flat-field dispersive monochromator or polychromator to create a spectrum. Individual points on the spectrum are then detected at different diodes or other detectors of the array of detectors. As an advantage of this technique, the many detections at various points along the spectrum may be made simultaneously, which provides a significant improvement over a scanning monochromator-based instrument with a single detector, where measurements are sequentially made along the spectrum of luminescence.

One disadvantage of diode array detectors, for example, is that they are generally less sensitive than photomultiplier tubes, since in a diode array a photon can produce only one charge while a photomultiplier tube can have a high electron gain. Also, diode arrays are electronically noisier than photomultipliers, and the dynamic range of diode arrays is less than photomultipliers. Optical array detectors and CCD cameras have been used for more than a decade by several companies in equipment designed for steady-state luminescence measurements (for purposes of this application, the term "luminescence" is intended to include fluorescence). The reading of the device in such analyzers, i.e. The measurement of the intensity of each element of the array, is performed sequentially. Some devices allow random addressing of elements of the array. Thus, it takes a substantial amount of time to read the content of the entire array. The fastest linear array can be read in a fraction of a millisecond, but normally the entire array can be read at a rate of no more than about a hundred times a second. Thus, spectral or spatial variations that occur in a faster time scale than this can not be directly recorded using these devices.

To measure fast spectral changes, for example in the nanosecond range, the above devices may be generally coupled with a fast, gatable, proximity-focused image intensifier. The gain of the intensifier can be changed very rapidly, i.e., in a few nanoseconds, providing a simple method to acquire a time slice or sampling of a repetitive, fast changing signal. The entire time evolution of the process can be measured by varying the delay between the start of the repetitive process and the opening of the gate of the image intensifier. Using this method, the time evolution can be recorded to the shortest time the gate can be opened, which is about five nanoseconds for most of the systems available. Recently, a new technique, based on a RF matched strip on the cathode of the micro-channel plate intensifier has been introduced with a time window of about fifty picoseconds. However, such a sampling method of data collection is very inefficient, since the overall duty cycle, i.e., the time of data collection relative to the total time of a measurement, is very small. For example, to acquire one hundred data points of a time varying process using a time slice of five nanoseconds results in a duty cycle of about $5 \times 10^{-7}$ seconds if the array can be read at a maximum speed of 100 Hz. Of course, the duty-cycle problem is not very severe for low repetitive pulsed laser sources, but it becomes of crucial importance when high repetition rate laser sources or sinusoidally intensity modulated sources are employed such as in the K2 Multifrequency Phase Fluorometer (MPF) made by I.S.S..

Recently, microchannel plate detectors (MCP) have been used also in frequency domain fluorometry and/or phosphorimetry. See, for example, Lakowicz, et al. "Gigahertz Frequency Domain Fluorometry: Applications to Picosecond Processes and Future Developments", *Time-resolved Laser Spectroscopy in Biochemistry*, edited by J. R. Lakowicz, Proceedings S.P.I.E., Vol. 909, p.15–22, (1988); Laczko, et al., "A 10-GHz Frequency-Domain Fluorometer", *Rev. Sci. Instrum.*, Vol 61, pp. 2332–2337, (1990). The MCP-PMT response to short-lived phenomenon is much better since the spread in electron paths in such devices is much less. Typical frequency response ranges to 3 GHz (50% response point) for 6 micron MCP tubes. However, their high internal resistance precludes the use of internal heterodyning although one attempt was made, Berndt, K. W., et al., "4-GHz Internal MCP-Photomultiplier Cross-correlation", *Rev. Sci. Instrum.*, Vol 61, pp. 2557–2565, (1990). One of the drawbacks of non-imaging, photomultiplier tube detectors is their inability to simultaneously process the various regions of a spectrum. One can select various emission wavelengths and obtain spectrally resolved luminescence lifetime information by the above prior art. However, the procedure is quite time consuming since only one emission wave length is acquired at a time.

Micro-channel plate detectors have been used in frequency domain fluorometry and/or phosphorimetry as image intensifiers in Gratton et al., "Parallel Acquisition of Fluorescence Decay Using Array Detectors", *Time-resolved Laser Spectroscopy in Biochemistry II*, edited by J. R. Lakowicz, Proceedings S.P.I.E., Vol 1204, part 1, p. 21–25 (1990). In this article, the radio frequency gain modulation of a gatable, proximity-focused micro-channel plate image intensifier is optically coupled to a diode array of 512 elements. This system is used with a light source amplitude modulated in the MHz range. Equivalent time-resolution of this instrument is about 100 ps. The frequency response of the instrument was 100 MHz. High frequency information, in the MHz region, is down converted into a low frequency signal of several to tens of Hz by way of internal gain modulation of the detector as discussed in Gratton and Limkeman, "A Continuously Variable Frequency Cross-Correlation Phase Fluorometer with Picosecond Resolution", *Biophysical Journal*, Vol. 4, p. 315–324 (1983).

This method provides a simple way to conveniently and accurately determine phase and modulation at high frequencies in the MHz range. From the phase and modulation values, the characteristic relaxation times of the system under investigation can be easily obtained using standard methods. A slow readout diode array or charge coupled device detector (with a maximum frame-transfer readout speed of 60 Hz) is combined with the frequency down-conversion capabilities of a fast-gain-modulated proximity-focused image intensifier. Modulation frequencies of the intensity modulated light source and the gain modulated detectors differ by an amount of this cross-correlation or heterodyning frequency. This low frequency signal thus produced by the cross-correlation or heterodyning passes through the phosphor screen, which has a frequency response maximum of about 1 KHz.

The above articles comprise the first description of the use of single-step, internal cross-correlation heterodyning with an array detector in multifrequency phase fluorometry. Such a gain-modulated array detector system overcomes the low duty cycle and some disadvantages of other non-imaging detector systems. As described in Feddersen et al., the system cannot be used other than at selected modulation frequencies and in a relatively narrow range of frequency. The main problem is the strong radio frequency interference of the system and the low integration capability.

By this invention, an apparatus and method for cross-correlation frequency domain fluorometry-phosphorimetry is provided which exhibits significant improvements in the speed of data acquisition at multiple points across a luminescence spectrum. Thus, the apparatus of this invention can be used to derive data from a decaying spectrum under non-steady state conditions in a manner showing significant improvements over detectors of the prior art. Time resolutions in the picosecond time range may be achieved when modulation frequencies in accordance with this invention are in the 100 to 200 MHz range, so that transient, unstable luminescence phenomena may be studied. Also, the problems arising from radio-frequency interference present in the apparatus described by Gratton et al. are here completely resolved by use of a novel double modulation scheme.

DESCRIPTION OF THE INVENTION

In accordance with this invention, apparatus for cross-correlation frequency domain fluorometry-phosphorimetry is provided, which apparatus comprises a source of electromagnetic radiation plus means for amplitude modulating the electromagnetic radiation at a first frequency. Means are also provided for directing the amplitude-modulated electromagnetic radiation at a sample.

Optical array detectors means are provided for detecting the luminescence of the sample. Means are present for providing a signal coherent with the amplitude modulated signals produced by the above cited amplitude modulating means, at a second frequency, the second frequency being different from the first frequency, for example typically by about 10 to 100 Hz.

Means are also provided for shutting off and turning on the coherent signal providing means at the second frequency mentioned above in a cycle of shutting off and turning on at a third frequency that is different from the difference between the first and second frequencies. This produces a resultant signal at a frequency derived from the difference and the third frequency.

Means are also provided for modulating the gain of the microchannel plate image intensifier mounted in front of detecting means, or multiplying the output of said detecting means, as may be appropriate for the particular detecting means used, by means of the resultant signal when the resultant signal is in its turned-on phase.

Means are provided for reading the amount of luminescence detected by the optical multi-channel analyzer detecting means in its various channels when the coherent signal providing means is off in its cycle of the third frequency.

Then, second means are provided for detecting a signal from the reading means described above, at a frequency of the resultant signal, to determine phase shifts and modulation changes of the luminescence.

Preferably, the frequency of the resultant signal may be about 1 to 10 Hz. The difference between the first and second frequencies may preferably be essentially 6 to 40 Hz. The first frequency is preferably essentially 10 to 200 MHz. When the first frequency is that high, transient luminescence decay modes may be detected and analyzed in a manner which is not possible with apparatus of the prior art. Preferably, the diode array detector analyzer means may include a micro-channel plate image intensifier linked with a diode array detector, although other equivalent devices, such as CCD and CID cameras, may also be used in accordance with this invention.

DESCRIPTION OF SPECIFIC EMBODIMENTS

Figure 1:
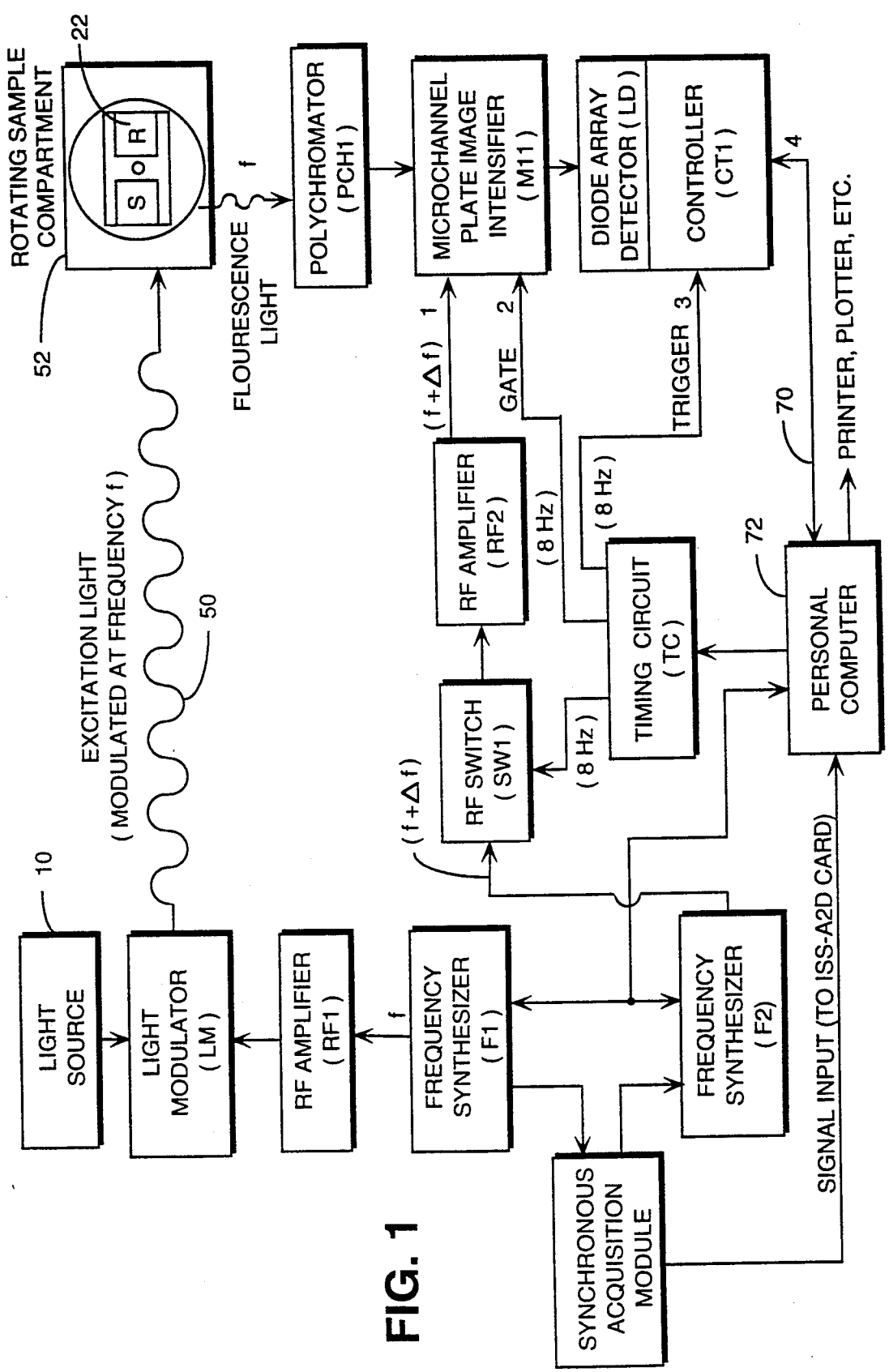
FIG. 1 is a flow chart for one embodiment of the apparatus of this invention showing various functional parts thereof.

Referring to the drawings, the apparatus of this invention may be broadly similar to the apparatus as disclosed in Gratton U.S. Pat. No. 4,840,485, and particularly the apparatus disclosed in Gratton, et al. U.S. patent application No. 07/807,261, filed Dec. 13, 1991 and entitled High Speed Cross-Correlation Frequency Domain Fluorometry-Phosphorimetry, now U.S. Pat. No. 5,212,386 but modified with the improvements disclosed herein.

Referring to FIG. 1, a light source may be a continuous wave laser or a collimated coherent or incoherent DC light source such as an arc lamp, for example. Light from light source 10 passes through light modulator LM, such as a Pockels cell, to provide a beam of excitation light 50 modulated at frequency f, typically at high frequency such as 100 MHz, for an improved collection capability of transient luminescence data. Modulated light 50 enters rotating sample compartment 52, which comprises a conventional turret to irradiate one of the samples S held therein. The turret can then shift by 180 degrees to irradiate a reference sample 22.

Unlike the previously cited references, the particular apparatus specifically disclosed herein does not utilize a beam splitter of the beam or a reference photomultiplier or other light collector, the reference function being provided by the reference material in the rotating sample compartment.

First frequency synthesizer F1 is locked in phased relation with second frequency synthesizer F2, appropriate frequency synthesizers being commercially available. Frequency synthesizer F1 imposes the first frequency on Pockels cell LM through RF amplifier RF1 which, Pockels cell LM, in turn, produces the modulated beam of light 50 at the first frequency. Beam 50 may be carried by a fiber optic bundle if desired.

Second frequency synthesizer F2 communicates through RF switch SW1 with RF amplifier RF2, providing a second frequency through amplifier RF2 that is typically about 10 Hz greater than the first frequency. Frequency synthesizer F2 may be phase-locked to frequency synthesizer F1 through the synchronous acquisition module, which may be a conventional electronic card, more particularly described in the prior application serial No. 07/807,261 U.S. Pat. No. 5,212,386.

Figure 3:
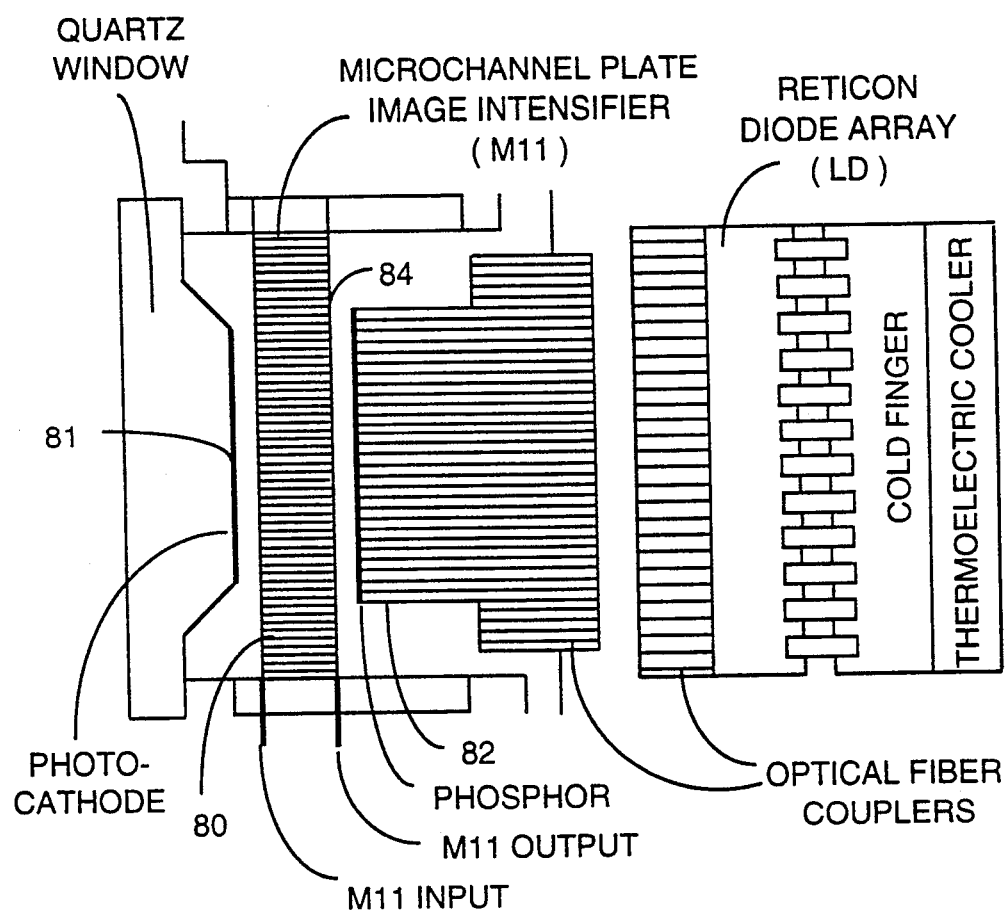
FIG. 3 is a further detailed, schematic view of the microchannel plate image intensifier and diode array detector, showing the electron intensifier component thereof as well as the diode array and other parts.
Figure 5:
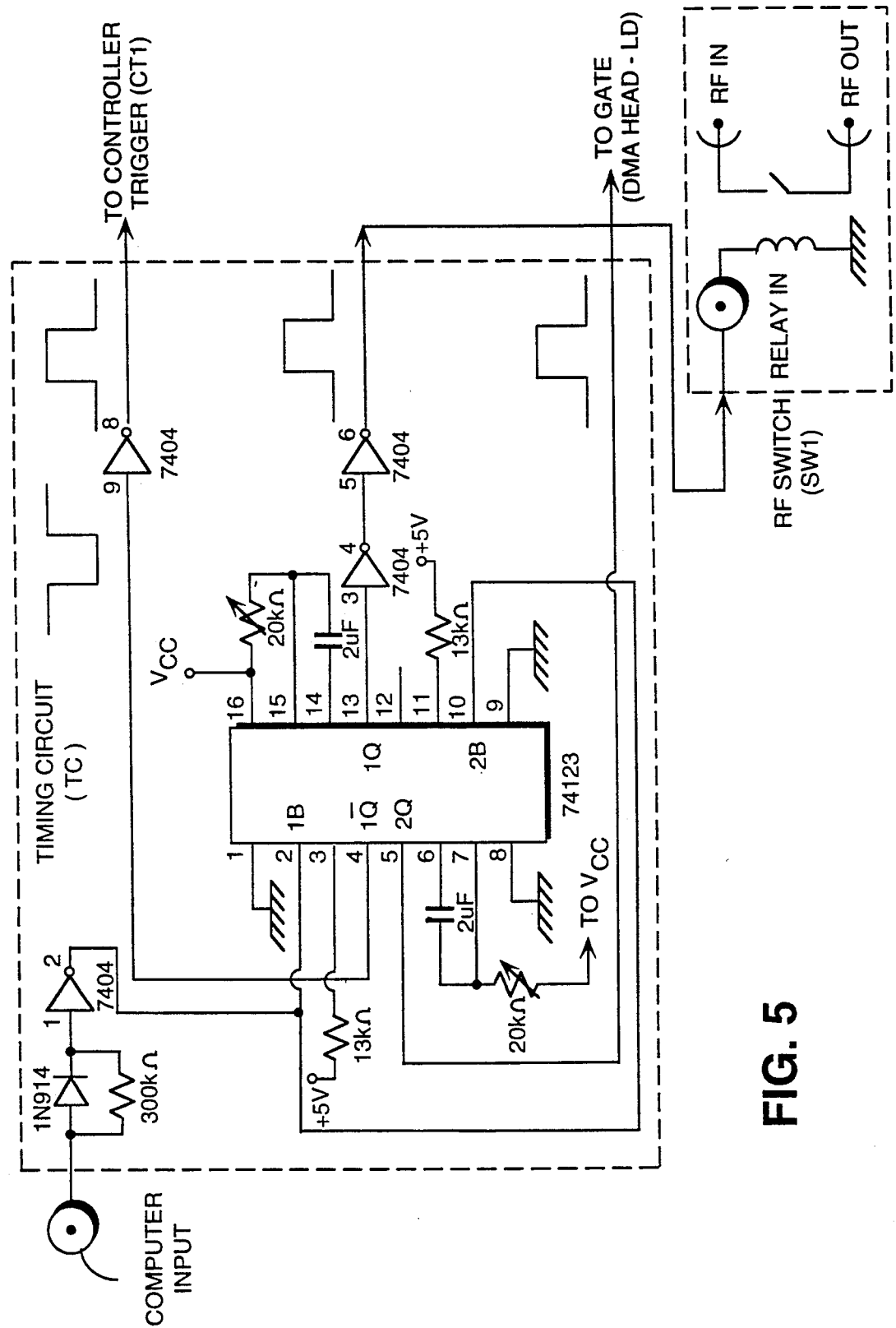
FIG. 5 is a circuit diagram of the timing circuit of FIG. 1.

Timing circuit TC controls RF switch SWI, through electronics as shown in FIG. 5, to impose an 8 Hz on and off cycle for switch SW1, which of course imposes an intermittent production of signal from RF amplifier RF2 to the photocathode of image intensifier MII, shown more particularly in FIG. 3. Timing circuit TC also sends the same, synchronous 8 Hz signal to the gate 2 of the head of the image intensifier MII as shown and the same signal to the trigger of controller CT1 of the diode array detector through gate 3.

Figure 2:
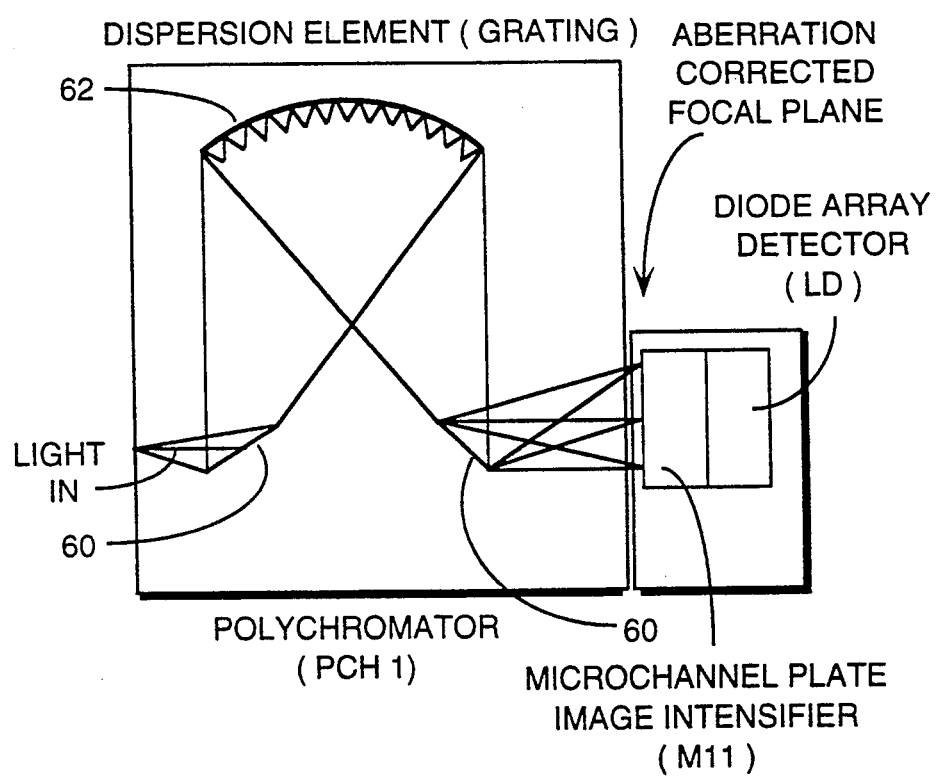
FIG. 2 is a detailed, schematic view of the polychromator, microchannel plate image intensifier and diode array detector components of FIG. 1.

Fluorescence from the sample, excited by light beam 50, and therefore modulated at the first frequency, is received by the polychromator shown particularly in FIG. 2. Mirror 60 first receives light and sends it to dispersion grating 62, from which the dispersed light in the form of a spectrum is reflected by a second mirror 60 to the photocathode surface of the microchannel plate image intensifier where the light flux is converted into electrons. The different spatial location of each wavelength (image) is transferred at the exit of the MII where the diode array detector is located, so that each individual diode simultaneously senses a different portion of the fluorescence spectrum. The diode stores electric charge in a manner responsive to the intensity of the light sensed. The respective charges stored in each diode may then be measured and data corresponding thereto may be transmitted through signal output 70 (FIG. 1) to personal computer 72 for processing. This processing may be in a manner as more fully described in the previously cited patent application no. 07/807,261.

The microchannel plate image intensifier MII and the diode array detector LD, are basically conventional.

The design of the MII typically limits the ultimate time resolution of the system, and thus a high quality image intensifier and diode array can provide improved performance. Typically, a single stage, proximity-focused micro-channel plate image intensifier may be used as the electron intensifier of this invention. When light from the polychromator PCH1 impinges on the photocathode of FIG. 3 (which may be type S20-extended) it will typically extract one electron. This electron is accelerated by the voltage difference between the cathode and the micro-channel plate input face 80. Once the electron enters the micro-channel plate 80 it is further accelerated by collisions with the walls of the conventional micro-channel tube, called the "intensifier", to produce a cascade of electrons, each cascade containing generally about 10,000 electrons. These electron packets at the micro-channel output face 84 are further accelerated to strike a phosphor screen 82, where a light image is produced. The phosphor screen 82 is optically coupled to a linear detector using an optical fiber face plate labelled as a "Reticon Diode Array".

The double-scheme modulation process (superheterodyning) is accomplished as follows. The fluorescence light beam impinging on the photocathode of the microchannel plate image intensifier MII is modulated at the first frequency f. The gain of the microchannel plate image intensifier MII is modulated through gate 1 at a frequency [Δf] provided by RF amplifier RF2. This signal is turned on and off at a 8 Hz rate by switch SW1 to avoid radio frequency pickup noise (see in the following). Thus, the electron packets generated by the photocathode arrive at the input 80 of the image intensifier at frequencies 2f and Δf, each at a 8 Hz rate. Only the signal at low frequency DF, typically at 10 Hz, is considered. This 10 Hz resulting signal is further chopped at a 8 Hz rate (gate 2) by the transistor T1 of FIG. 4, giving a resultant signal at a frequency of 2 Hz. This 2 Hz resultant signal is the modulation of the electron packets at the exit of the MII and impinging the phosphor; hence, the light produced by the phosphor located at the output of the microchannel plate image intensifier, and eventually detected by the diode array detector is also modulated at 2 Hz. Therefore, by changing the voltage between the photocathode and the micro-channel plate input, the gain of the intensifier can be changed by several orders of magnitude. Modulation depths with a peak-to-peak voltage of about 20 volts and a 10 volt bias can be about 90 percent.

Figure 4:
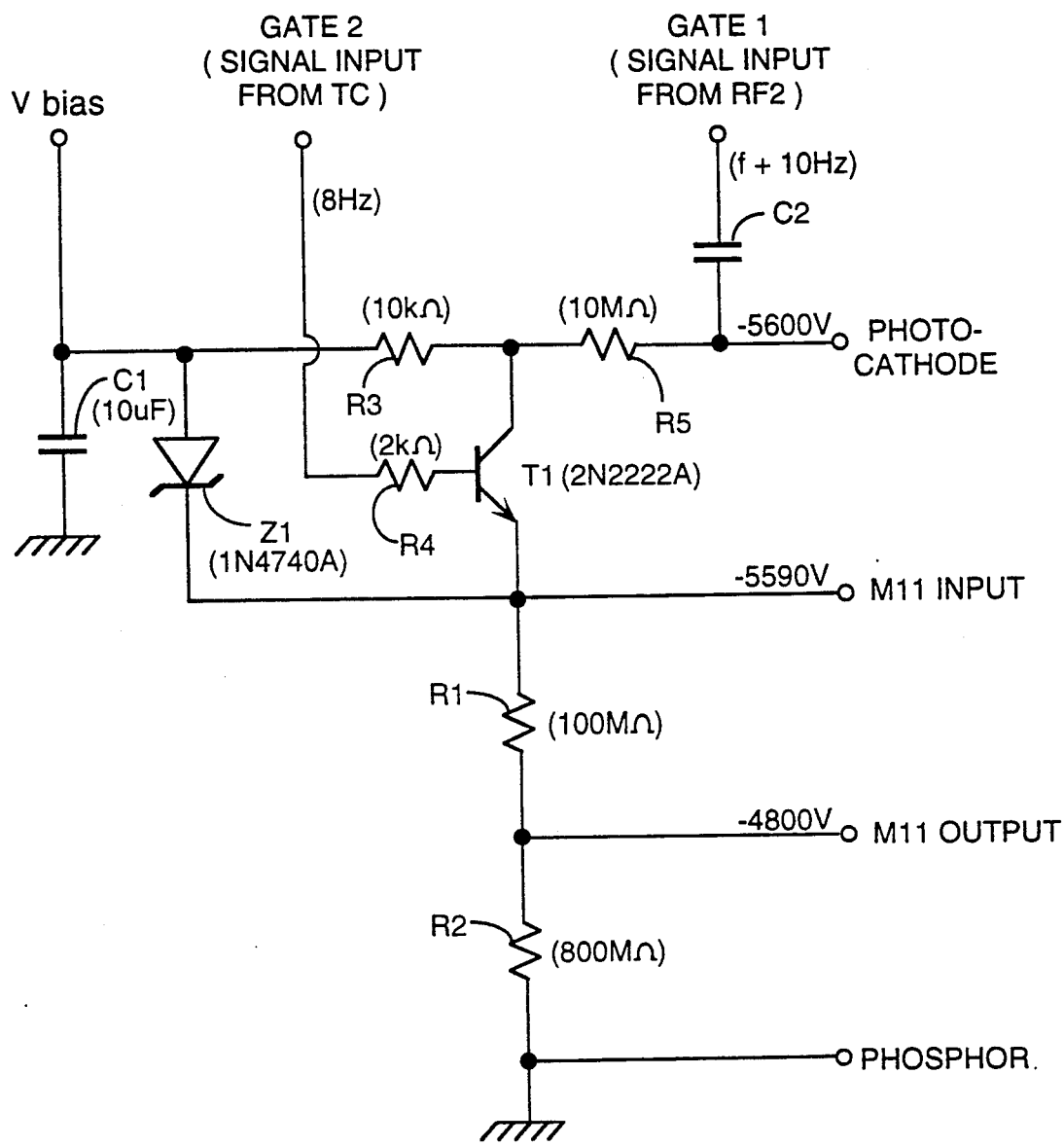
FIG. 4 is a circuit diagram of circuitry for the modulation of the gain of the micro-channel plate image intensifier and diode array detector.

Referring to FIG. 4, an electronic circuit is shown which comprises a biasing circuit for the microchannel plate intensifier (MII) of FIG. 3, and two switches to turn MII on and off via gate 2 (FIG. 1) and also to shut off the RF signal via switch SW1. The RF signal is applied to capacitor C2 to decouple the RF signal from the biasing voltage. The value of zener diode Z1 is chosen to obtain the best modulation of the intensifier MII for a given radio frequency level. Transistor T1 acts as a switch to turn on and off MCP intensifier MII. When the transistor is conducting, the voltage between the cathode and the MII input is about zero, which results in no electron acceleration, preventing electrons from the cathode 81 from reaching the input face of MII 80.

The gate signal input from timing circuit TC is an 8 Hz signal entering through gate 2, while the input from RF2 entering from gate 1 is at a frequency [f+(10 Hz)]. Thus, their passes through resistor R1 produce a resultant pair of signals respectively at 2 and 18 Hz. Proper timing of timing circuit TC is achieved with the circuit of FIG. 5, which also shows the control of RF switch SW1.

The connections entitled "MII input", "MII output" and "phosphor" are connections to conventional terminals of a conventional microchannel plate image intensifier.

The terminal entitled "$V_{bias}$" connects to a constant voltage, the value of which helps to determine the depth of the modulation of the system.

The RF signal from amplifier RF2 is at a frequency [f+10 Hz] and it is applied to the location labelled "input (from RF2)" in FIG. 4. This RF signal produces a first heterodyning step of the signal down to 10 Hz. An 8 Hz square wave signal is applied to port 2 of the diode array detector head LD, shown as "gate 2" (signal input from TC) in FIG. 4. The gate signal is generated from pin 5 of the integrated circuit numbered 74123 of FIG. 5. The detector is chopped at 8 Hz, thus producing a 2 Hz heterodyning signal from the 10 Hz light signal at the output of the MII.

The diode array as disclosed in FIG. 3 is a known device which intrinsically integrates photons of light sensed. A photon impinging on one element of the diode array detector LD produces a charge separation with an efficiency of about 40 percent. The detector element stores the charge until the detector is read. The 2 Hz signal only is read by the personal computer through signal output 70. Reading of the charge accumulated in the detector LD is accomplished by measuring the amount of charge necessary to discharge each detector element. Best performance of the detector is obtained by accumulating enough charge as compared with the intrinsic charge leak of each element, with the charge of course not exceeding the maximum element charge capacity. Thus, there is a need to slow down the detector reading speed to match the conditions for best signal-to-noise ratio as may be accomplished by this present invention.

The detector is read four times per period of 2 Hz, which requires again an 8 Hz signal. The trigger for detector reading is applied at input 3 of controller CT1 (FIG. 1), the signal for which is generated by pin 4 of the integrated circuit 74123 of FIG. 5.

Figure 6:
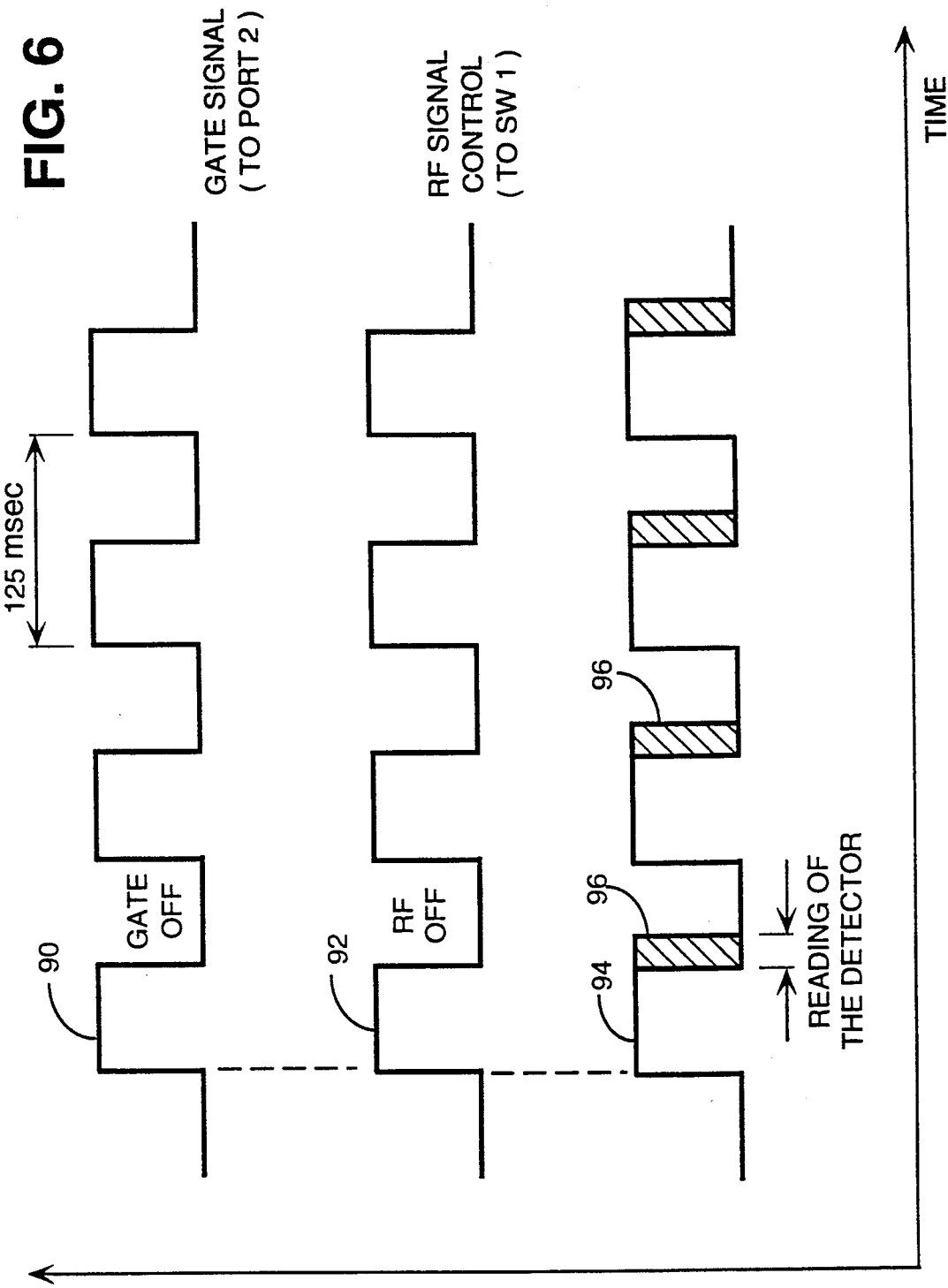
FIG. 6 is a chart showing the timing of the signals delivered by the timing circuit to the gate (port 2) of microchannel plate image intensifier and the RF switch. Also, the timing at which the reading of the diode array detector is performed (by the controller) when the gate and RF switch are in the "off" mode, is shown.

During the detector reading phase, the RF signal to controller CT1 is turned off by the relay circuit of FIG. 5. Thus, in FIG. 6, the gate signal from timing circuit TC to port 2 of diode array detector LD is shown by square wave 90, the wave period being 125 milliseconds or 8 Hz. The second square wave array 92 represents the RF signal sent from the timing circuit TC to the switch SW1 so that the RF signal through amplifier RF2 is on and off in an alternating, square wave pattern which is synchronous with square wave 90.

Then, in square wave pattern 94 the diode array detector LD is read as controlled by the trigger circuit from timing circuit TC to port 3 of the controller CT1. Immediately after the shut off of the gate signal to port 2 and switch SWI, there is a brief reading time 96 in which the detector LD reads light from polychromator PCH1 without RF interference.

Thus, by this invention, a low frequency signal is generated from the high frequency light signal impinging on the photocathode of the microchannel plate image intensifier MII. This frequency conversion results in a slow variation of the intensity of the light at the phosphorous screen 82. The low frequency signal is a replica of the signal at high frequency that impinges on photocathode 81, and it carries the information on the fast process to be measured. The modulation of the gain of the electron intensifier accomplishes this goal if the frequency used to modulate the gain is close but not equal to the frequency of the fast varying signal at each diode array element (or other array element if another is used).

The low frequency signal has a sinusoidal varying intensity. To fully characterize the sinusoidal wave at each element, it is needed to determine its average value (DC), the amplitude (AC) and the phase (P). In this particular embodiment, the sinusoidal signal is sampled typically 4 times per wave period, although other numbers of samplings may of course be used, preferably ranging from about 4 to 16. The DC, AC and P values are determined using the following formulas:

$$DC = \tfrac{1}{4}(I_1 + I_2 + I_3 + I_4) \qquad [1]$$

$$AC = [(I_1 - DC)^2 + (I_2 - DC)^2]^{\tfrac{1}{2}} \qquad [2]$$

$$P = \tan^{-1}\{(I_1 - DC)/(I_2 - DC) \qquad [3]$$

where $I_1$, $I_2$, $I_3$ and $I_4$ are the four values of the intensities sequentially read at four different times during the one period of the sinusoidal wave, at 0, 90, 180, 270 degrees.

Frequency synthesizers F1 and F2 thus can generate two frequencies that differ by a minimum of, typically, 10 Hz in the range of 10 KHz to 1000 MHz. The period of a 10 Hz wave is 100 milliseconds. Since one needs to read the entire detector for example four times during this period of the 10 Hz wave, the minimum detector reading speed in that case is 25 milliseconds. Most linear array detectors can be read in less than 10 milliseconds. However, the radio frequency signal used to modulate the intensifier must be turned off during the reading of the detector due to excessive radio frequency pickup, decreasing the duty cycle of the light measurement process. This turning off of the RF signal during the process has been described above. Furthermore, during 25 milliseconds, the total charge accumulated in the detector can be relatively small resulting in inefficient use of the integrating detector. To avoid this latter problem and to make good use of the necessity to turn off the radio frequency signal during the reading process, by this invention a two step heterodyning process may be used. In the first step, the high frequency signal which may be in the megahertz range is converted down to 10 Hz by the use of the two frequency synthesizers F1, F2. In a second step, the 10 Hz signal is further down converted to 2 Hz by the use of the 8 Hz signal from the timing circuit, providing the 2 Hz resultant signal with respect to the 10 Hz differential signal from RF amplifier RF2. This superheterodyning scheme results in an efficient use of the detector, improved signal-to-noise ratio, and total rejection of the radio frequency disturbance. The entire electronic circuit for the second heterodyning step can be built using simple electronics as shown plus a relay to switch off the radio frequency, and a transistor to modulate the gain of the electron intensifier 80.

To properly operate the optical multi-channel analyzer 58 in the frequency domain, it is necessary to know the exact time that each element (i.e. each diode) of the array is read. Since the array is read sequentially there is an intrinsic phase delay between different elements (diodes). The time delay between two consecutive elements of the array is exactly known since it corresponds to the sampling time, which can depend on a clock of an A/D converter in conventional circuitry. Also, the four sampled values of the signal over time of each diode in the array are known, as previously described, if the intensities of one period are read in response to an external trigger. Therefore the delay between different elements and the time at which the array is read is exactly known, and the data processing software can be conventionally programmed to account for these delays.

The frequency response of the specific embodiment shown performs well up to a first frequency provided by frequency synthesizer F1 of up to about 210 MHz. By this invention, one can determine the absolute value of the signal lifetime at each array element or diode. The phase of the sinusoidal varying intensity of the signal from polychromator PCH1 at each diode element of the array is known relative to one of the diode elements, for example, the first element of the array. By this invention the phase delay of the optics and of the electronics is calibrated in conventional manner to calculate the value of the phase relative to the phase of the excitation. The measurement of the phase modulation of a reference signal from a reference sample in rotating sample compartment 52 can accomplish this operation as compared with the sample being tested.

For example, in fluorescence it is assumed that the scattered light has the same phase as the excitation light beam 50. The signal corresponding to this scattered light, which passes through polychromator PCH1, is easily recognized and measured by optical diode array detector LD. Otherwise, a signal that has a known delay can also be generated using a fluorescent lifetime standard. Thus, the lifetime spectrum of a relatively weak fluorescent sample can exhibit superior sensitivity obtained using the frequency domain superheterodyning scheme of this invention.

For example, when a reference compound is a solution of p-terphenyl in cyclohexane, an entire lifetime spectrum of a protein in a solution can be acquired in about 40 seconds. The sample has a fluorescence lifetime of about 3 nanoseconds.

Polychromator PCH1 may be a flat field HR320 polychromator with 150 grooves per millimeter, ruled grating made by instruments S.A. Inc. of Edison, N.J. The microchannel plate image intensifier MII (58) and diode array of detector LD may be a model IPDA-1024 GRB, 5 nanosecond fast-gate, intensified diode array with a proximity-focused intensifier made by Princeton Instruments, Inc. of Trenton, N.J.

Controller CT1 may be a model ST121 optical multichannel analyzer controller made by Princeton Instruments. The light source, the light modulator LM and the rotating sample compartment may be contained in a K2 Multifrequency Phase Fluorometer made by I.S.S. Inc. If desired, the light source and light modulator LM may be replaced by a mode-locked laser, making use, for example of a KOALA $_{TM}$ Automated Sample Compartment sold by I.S.S. Inc.. In both the K2 and the KOALA, the fluorescent light emitted by the sample is sent to the polychromator by optical fiber couplers, made of two meter long, 3 millimeter diameter quartz fiber optic bundles made by C-Technologies of Verona, N.J.

Alternatively, a pulsed diode laser can be utilized, where the exciting light beam is brought directly to the sample by means of a fiber optic assembly. Such a device can be utilized as a sensor of different processes such as physiological monitoring of oxygen concentration, physiological monitoring of drug delivery, industrial control processes or the like. Such a pulsed light source may produce an optical pulse train of 5 picoseconds pulses at a base repetition rate of 7.62 MHz, for example. From the Fourier principle, it is known that such a pulse train will comprise a large series of harmonic signals in the frequency domain, having a harmonic content up to many GHz.

One mode locked laser system which may be used is a ND-YAG frequency-doubled model 76 ML-SHG neodymium-yttrium aluminum garnet laser mode-locked at 76.2 MHz, made by Coherent, Inc. of Palo Alto, Calif., where the mode-locked driver is phase-locked to frequency synthesizer F2 of FIG. 1.

Accordingly, apparatus for cross-correlation frequency domain fluorometry-phosphorimetry is disclosed which exhibits the capability of simultaneously measuring, over a wide wavelength range, the spectral dispersion of the lifetime of a fluorescence and/or phosphorescence sample. Through the frequency-domain technique, a high frequency modulated light source may be used for obtaining measurements of: the decay of fluorescence and/or phosphorescence; measurements of the anisotropy decay of fluorescence and/or phosphorescence; measurements of time-resolved spectra of fluorescence and/or phosphorescence; measurements of phase and modulation resolved spectra of fluorescence and/or phosphorescence; and measurements of lifetime kinetics of fluorescence and/or phosphorescence.

By this invention a microchannel plate image intensifier MII whose gain can be modulated at high frequency is coupled to the optical diode array detector. This capability provides a means to shift the high frequency signal that carries the lifetime information to a convenient, low frequency, signal. The low frequency signal has such a long period that it can be sampled typically at least four times per wave period by reading the entire array detector LD.

Further by this invention, a first heterodyning step followed by a second heterodyning step further increases the period of the low frequency signal. During this long period, enough charges are produced on the array detector (specifically the diode array) to minimize the effects of charge leakage and temperature induced charge separation (dark noise). This double or super-heterodyning process can provide an effective duty cycle on the order of about 0.5, specifically at least 0.4, which is comparable to the duty cycle of the diode array when used for steady state measurements. Thus, an improvement of about a million times can be obtained over a duty cycle obtained using the conventional-gating scheme of an intensifier (FIG. 3) by this invention.

In the specific embodiment of this invention, the gain of microchannel plate image intensifier MII can be modulated to a frequency as high as 210 MHz, limited by the particular microchannel plate image intensifier used. At this upper frequency the ultimate time resolution is about 5 ps corresponding to a phase shift of about 0.2 degree. This value is about 400 times better than the time resolution obtained using nanosecond gating of the image intensifier.

Electronic timing circuit TC generates the synchronization signals. The purpose of timing circuit TC is (a) to provide a trigger signal for reading the diode array detector through the port 3 of controller CR1; (b) to turn on and off the microchannel plate image intensifier through gate 2 with specifically and 8 Hz signal to produce the second heterodyning signal; and (c) to turn on and off the radio frequency signal of amplifier RF2 by means of a switch SW 1, to avoid RF interference in the microchannel plate during diode array reading, as specifically indicated by FIG. 6.

An acquisition system using personal computer 72: (a) automatically corrects for the intrinsic delay between the reading of successive elements of diode array LD; (b) compensates for the delay of the electronics to give a calibrated lifetime value; (c) displays the spectral dispersion of the lifetime superimposed on the spectral intensity.

To accomplish this, the photomultiplier tube of prior art systems is replaced by the optical diode array detector LD, which may, for example be a diode array, a CCD camera, or a CID camera.

As previously discussed, the light source may be an arc lamp, a spectral lamp, an LED, a continuous wave laser, a diode laser, or the like, with the light beam 50 being pulsed in a variety of possible ways. Optionally, the light source may be a mode-locked laser or a synchrotron.

The above has been offered for illustrative purposes only, and is not intended to limit the scope of the invention of this application, which is as defined in the claims below.

That which is claimed is:

1. An apparatus for cross-correlation frequency domain fluorometry-phosphorimetry, which comprises:
   a source of electromagnetic radiation;
   means for amplitude modulating the electromagnetic radiation at a first frequency;
   means for directing the amplitude-modulated electromagnetic radiation at a sample;
   optical array detector means for detecting the luminescence of the sample;
   means for providing a signal coherent with amplitude modulated signals produced by said amplitude modulating means, at a second frequency, said second frequency being different from said first frequency;
   means for shutting off and turning on said coherent signal providing means in a cycle having a third frequency that is different from the difference between the first and second frequencies, to produce a resultant signal at a frequency derived from said difference and said third frequency;
   means for modulating the gain of said detecting means, or multiplying the output of said detecting means, by said resultant signal;
   means for reading the amount of luminescence detected by said optical array detector means when said coherent signal providing means is off in its cycle of said third frequency; and
   second means for detecting a signal from said reading means at a frequency of said resultant signal to determine phase shift and modulation changes of said luminescence.

2. The apparatus of claim 1 in which the frequency of said resultant signal is about 1-10 Hz.

3. The apparatus of claim 1 in which said optical array detector means comprises a microchannel plate intensifier linked with a diode array detector.

4. The apparatus of claim in which the difference between the first and second frequencies is essentially 6-40 Hz.

5. The apparatus of claim 1 in which said first frequency is essential by 100 hertz to 300 megahertz.

6. The apparatus of claim 1 in which said resultant signal frequency is no more than about one quarter of the frequency difference between the first and second frequencies.

7. The apparatus of claim 1 in which said resultant signal frequency derived from said frequency difference and said third frequency by subtraction.

8. An apparatus for cross-correlation frequency domain fluorometry-phosphorimetry, which comprises:
   a source of electromagnetic radiation;
   means for amplitude modulating the electromagnetic radiation at a first frequency;
   means for directing the amplitude-modulated electromagnetic radiation at a sample;
   an image intensifier having a photocathode and a microchannel plate intensifier to amplify the luminescence of the sample;
   an optical array detector for detecting the amplified luminescence of the sample;
   means for providing a signal coherent with amplitude modulated signals produced by said amplitude modulating means, at a second frequency, said second frequency being different from said first frequency;
   means for shutting off and turning on said coherent signal providing means in a cycle having a third frequency that is different from the difference between said first and second frequencies.
   means to direct said second frequency signal to the photocathode of the image intensifier;
   means for producing a signal equal in frequency to said third signal to the input of the microchannel plate intensifier to modulate the gain of the image intensifier and produce a resultant signal at a frequency derived from said frequency difference and said third frequency;
   means for reading the amount of luminescence detected by said optical array detector when said coherent signal providing means is off in its cycle of aid third frequency; and
   second means for detecting a signal from said reading means at a frequency of said resultant signal to determine phase shift and modulation changes of said luminescence.

9. The apparatus of claim 8 in which the frequency of said resultant signal is about 1-10 Hz.

10. The apparatus of claim 8 in which said optical array detector means comprises a CCd and/or CID camera detector with image intensifier.

11. The apparatus of claim 8 in which the difference between the first and second frequencies is essentially 6-40 Hz.

12. The apparatus of claim 8 in which said first frequency is essentially 100 hertz to 300 megahertz.

13. The apparatus of claim 8 in which said resultant signal frequency is of no more than about one quarter of the frequency difference between the first and second frequencies.

14. The apparatus of claim 13 in which said resultant signal is at a frequency derived form said frequency difference and said third frequency by subtraction.

15. An apparatus for cross-correlation frequency domain fluorometry-phosphorimetry, which comprises:
- a pulsed source of electromagnetic radiation having a first pulsation frequency;
- means for directing the pulsed electromagnetic radiation at a sample;
- an image intensifier having a photocathode and a microchannel plate intensifier to amplify the luminescence of the sample;
- an optical array detector for detecting the luminescence of the sample;
- means for providing a signal coherent with pulsed signals produced by said pulsed source of electromagnetic radiation at a second frequency, said second frequency being different from said first frequency;
- means for shutting off and turning on said coherent signal providing means at the second frequency in a cycle having a third frequency that is different from the difference between the first and second frequencies;
- means to direct said second frequency signal to the photocathode of the image intensifier;
- means for producing a signal equal in frequency to said third signal to the input of the image intensifier to modulate the gain of the image intensifier and produce a resultant signal at a frequency derived from said frequency difference and said third frequency;
- means for reading the amount of luminescence detected by said optical array detector when said coherent signal providing means is off in its cycle of said third frequency; and
- second means for detecting a signal from said reading means at a frequency of said resultant signal to determine phase shift and modulation changes of said luminescence.

16. The apparatus of claim 15 in which said first frequency is essentially 100 hertz to 300 megahertz.

17. The apparatus of claim 15 in which the difference between the first and second frequencies is essentially 6–40 Hz.

18. The apparatus of claim 15 in which said optical array detector means comprises a CCD and/or CID camera detector with image intensifier.

19. The apparatus of claim 15 in which the frequency of said resultant signal is about 1–10 Hz.

20. The apparatus of claim 15 in which the resultant signal is at a frequency derived from said frequency difference and said third frequency by subtraction.

* * * * *